United States Patent [19]

Khan et al.

[11] 4,262,115
[45] Apr. 14, 1981

[54] METHOD OF PREPARATION OF 2-CHLORO-2-DEOXYSACCHARIDES

[75] Inventors: Riaz A. Khan, Sonning; Michael R. Jenner, Pangbourne, both of England

[73] Assignee: Talres Development (N.A.), Curacao, Netherlands Antilles

[21] Appl. No.: 85,779

[22] Filed: Oct. 17, 1979

[30] Foreign Application Priority Data

Oct. 18, 1978 [GB] United Kingdom ............... 41115/78

[51] Int. Cl.$^3$ ............................................... C07H 5/02
[52] U.S. Cl. ..................................... 536/122; 536/1; 536/4
[58] Field of Search ....................... 536/1, 4, 122, 119; 424/180

[56] References Cited

U.S. PATENT DOCUMENTS 4,117,224  9/1978  Khon et al. ........................... 536/122

OTHER PUBLICATIONS

Chemical Abstracts, vol. 84, 31328b, 1976.
Chemical Abstracts, vol. 85, 2289e, 1976.
Chemical Abstracts, vol. 77, 85005t, 1972.

*Primary Examiner*—Johnnie R. Brown
*Assistant Examiner*—Blondel Hazel
*Attorney, Agent, or Firm*—Ostrolenk, Faber, Gerb & Soffen

[57] ABSTRACT

A process for the preparation of a 2-chloro-2-deoxy-mono-, di- or oligo-saccharide comprises reaction of a mono-, di- or oligo-saccharide derivative having a free hydroxy group in at least 2- position and having the hydroxy group in at least the 1- and 3- positions protected from chlorination, with sulphuryl chloride in the presence of an organic base in a chlorinated hydrocarbon solvent at a temperature below −40° C. to form a chlorosulphate derivative with a chlorosulphate group in at least the 2-position, which chlorosulphate derivative is then reacted with lithium chloride in the presence of hexamethylphosphoric triamide to replace chlorosulphate groups with chlorine atoms to form a chlorodeoxy derivative, which chlorodeoxy derivative is then freed of unwanted protecting groups.

16 Claims, No Drawings

METHOD OF PREPARATION OF 2-CHLORO-2-DEOXYSACCHARIDES

This invention relates to the preparation of a class of chlorinated derivatives of sugars, in particular of mono-, di-, and oligo saccharides.

Derivatives of sugars are known in which various hydroxy groups are replaced by chlorine atoms. In general, replacement of the primary hydroxyl groups of a sugar molecule by chlorine atoms is well known and certain of the secondary hydroxyl groups have also been replaced by chlorine. One group of chlorodeoxy sucrose derivatives is known to be intensely sweet. These compounds have chlorine substituents at positions selected from the 4-,6-1'- and 6'-positions and are described in detail in, e.g., West German OS No. 2700036, corresponding to British patent application No.616/76.

Various methods are used for the chlorination of sugars, but to date it has proved difficult to introduce chlorine atoms into the 2-position of the sugar ring. The 2-position is taken to be the position immediately adjacent to the anomeric centre (conventionally numbered as the 1-position). One of the most investigated chlorination reactions is that of sulphuryl chloride. This reagent gives products in which primary hydroxyl groups are replaced by chlorine and secondary hydroxyl groups are either esterified by a cyclic sulphate or substituted by chlorine with inversion of configuration (see, e.g. L. Hough, "Sucrochemistry," Am.Chem.Soc.-Symp.Series, 41 (1976) 9–21). However, a common feature in all reports on this topic is that the 2-hydroxyl group is inert to replacement. As an analogy, a similar lack of reactivity has also been observed in the replacement of 2-sulphonic ester groups of methyl glucopyranoside and methyl mannopyranoside derivatives. This lack of reactivity has been ascribed to unfavourable alignments of dipoles in the transition state of the reaction.

2-Halo-2-deoxy-hexose derivatives with protecting groups at the 1,-4- and 6-positions have been prepared as intermediates in the preparation of 2-deoxy compounds, by formation of a 2,3-epoxy ring, and opening it with a halogen acid (Rodd, Chemistry of Carbon Compounds, Vol.1F, p.507). These halo derivatives were, however, dehalogenated while still protected at the 1-,4- and 6-positions.

We have now found that, using particular controlled conditions, sulphuryl chloride can be used to obtain 2-chlorosulphate derivatives which can, again under controlled conditions, be reacted to give the 2-chlorodeoxy derivative with inversion of configuration.

According to the present invention, there is provided a process for the preparation of a 2-chloro-2-deoxy-mono-, di- or oligo-saccharide, comprising reaction of a mono-, di- or oligo-saccharide derivative having a free hydroxy group in at least the 2-position and having the hydroxy group in at least the 1- and 3-positions protected from chlorination, with sulphuryl chloride in the presence of an organic base in a chlorinated hydrocarbon solvent at a temperature below $-40°$ C. to form a chlorosulphate derivative with a chlorosulphate group in at least the 2-position, which chlorosulphate derivative is then reacted with lithium chloride in the presence of a polar aprotic solvent to replace chlorosulphate groups with chlorine atoms to form a chlorodeoxy derivative, which chlorodeoxy derivative is then freed of unwanted protecting groups.

The 2-chloro-2-deoxy-mono-, di-, or oligo-saccharides prepared may possess a single chlorine atom at the 2-position, or may additionally contain chlorine substituents replacing hydroxy groups at other positions. The 2-chloro-deoxy-mono-saccharides preferably comprise pentoses or hexoses which may be in pyranose or furanose-forms. A typical example is 2-chloro-2-deoxy-mannose, obtained from the corresponding glucose derivative with inversion at the 2-position.

2-chloro-2-deoxy disaccharides may preferably comprise a base unit which is a pentose or hexose and which may be in a pyranose or furanose form, together with an aglycone which is also a pentose or hexose in the pyranose or furanose form. The aglycone may itself carry chlorine substituents especially in the primary positions. The base unit may thus, for example, be a glucose, galactose or mannose ring and the aglycone may, for example, be a glycose or fructose ring. 2-chloro-2-deoxy-mannosucrose derivatives are of particular interest and examples include 2-chloro-2-deoxy-mannosucrose, 2,1'-dichloro,2-1'-dideoxy-mannosucrose and 2,6,1',6'-tetrachloro-2,6,1',6'-tetradeoxy-mannosucrose, obtained from the appropriate sucrose derivatives. 2-chloro-2-deoxy-oligosaccharides (i.e. saccharides with 3 to 10 ring units) include trisaccharides based on pentose or hexose units in the pyranose or furanose form. Typical sugars of this type include raffinose which has a galactose base unit coupled to a sucrose aglycone.

One important use of the 2-chloro-2-deoxy monosaccharides according to the present invention is in the preparation of 2-deoxy monosaccharides. In particular, a 2-chloro-2-deoxy-mannose or glucose derivative can yield, on removal of the chlorine atom, 2-deoxy glucose, i.e. 2-deoxy-α-D-arabinohexopyranose. This latter compound is now of use in the treatment of genital herpes (see J.Am.Med.Assoc.,241, 2798 (1979). 2-Deoxy sugars can be prepared from 2-chloro-2-deoxy sugars by treatment with a reagent serving to remove the chlorine atom and replace it with a hydrogen atom, e.g. a reducing agent of the type such as hydrazine hydrate in the presence of Raney nickel.

The most interesting of the 2-chloro-2-deoxy disaccharides is the novel compound 2,6,1',6'-tetrachloro-2,6,1',6'-tetradeoxy-mannosucrose which is a potent bittering agent comparable with quinine. In taste panel comparisons, the absolute taste threshold for quinine sulphate was found to be 19.3 ppm and for the tetrachloro-mannosucrose, it was found to be 20 ppm. This compound is thus of use in the replacement of quinine in food products, in particular soft drinks such as Indian tonic water. This compound's use is the subject of a co-pending patent application. Other 2-chloro-mannosucrose derivatives are useful in the preparation of the tetrachloro derivative. Thus, conventional chlorination of 2-chloro-2-deoxy-mannosucrose or 2,1-dichloro-2,1'-dideoxy-mannosucrose results in chlorination of the primary positions to give the required tetrachloro derivative. Also, 2-chloro-2-deoxy mannosucrose can be hydrolysed to give 2-chloro-2-deoxymannose.

2,1',6,6'-tetrachloro-2,1',6,6'-tetradeoxymannosucrose, 2-chloro-2-deoxymannose, 2,1'-dichloro-2,1'-dideoxymannosucrose and 2-chloro-2-deoxy-mannosucrose are also novel compounds and comprise a further feature of the present invention namely:

A compound of the general formula

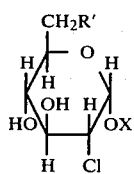

where X represents a hydrogen atom and R' represents a hydroxy group; or X represents an aglycone of the general formula

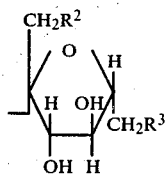

where $R^2$ represents a chlorine atom and $R^3$ represents a hydroxy group, or $R^2$, $R^3$ and $R^1$ all represent chlorine atoms.

In general, the starting material for the 2-chlorination reaction according to the present invention should have protecting groups on all hydroxy groups which are not intended to be chlorinated. Conventional protecting groups include carboxylic esters, e.g. acetates or benzoates; or ethers, e.g. alkyl pyranosides such as methyl pyranosides, and cyclic acetals such as 4,6',-O-benzylidene derivatives. Alternatively, certain positions on the sugar ring may already be chlorinated. Thus, for example, 6,6'-dichloro-6,6'-dideoxy sucrose carrying ester groups in the 3-,4-, 3'-, and 4'-positions can be chlorinated according to the present invention to provide 2,6,1',6'-tetrachloro-2,6,1',6'-tetradeoxy-mannosucrose.

Unwanted protecting groups, such as esters and ethers can be conveniently removed at the end of the reaction by conventional methods known per se including hydrolysis and hydrogenolysis. Other substituents such as chlorine atoms can remain if desired.

The organic base used in the reaction with sulphuryl chloride is conveniently a tertiary amine capable of binding the hydrogen chloride released in the reaction and dissolving the sugar derivative used as starting material. A preferred class of amines includes those with a pyridine ring, especially pyridine itself. The chlorinated hydrocarbon should preferably have a melting point in the presence of the base sufficiently low to permit reaction at a temperature below $-40°$ C. Chloroform is most preferred, although ethylene dichloride and dichloromethane are of interest. Particularly useful is a mixture of chloroform and pyridine in a volume ratio of 2.5:1 to 3.5:1, preferably about 3:1.

The reaction temperature is preferably as low as possible and a temperature of about $-70°$ C. is preferable.

The reaction of the chlorosulphate with lithium chloride should be effected in the presence of an apotic solvent, in particular an amide solvent such as dimethyl formamide or, most preferably, hexamethyl phosphoric triamide (H.M.P.T.), optionally in the presence of another polar aprotic solvent (such as dimethyl-formamide) in the case of H.M.P.T. The reaction is conveniently effected at a moderately elevated temperature, e.g. from 40° to 100° C., preferably at about 70° C.

The following Examples illustrate the invention further.

EXAMPLES

EXAMPLE 1

2-Chloro-2-deoxy-mannose (a) Methyl 3-O-acetyl-4,6-O-benzylidene-α-D-glucopyranoside 2-chlorosulphate (2)

A solution of methyl 3-O-acetyl-4,6-O-benzylidene-α-D-glucopyranoside (6.2 g) (R. Khan, Carbohydr.Res., 25 (1972) 504–510). (1) in chloroform (90 ml) and pyridine (30 ml) was treated with sulphuryl chloride (7.5 ml) at $-75°$, and then warmed slowly to $-40°$ over 45 min. The reaction mixture was poured into ice-cold sulphuric acid (10%, 500 ml) with vigorous shaking and then extracted with dichloromethane. The organic layer was washed successively with water, aqueous sodium hydrogen carbonate and water, and dried ($Na_2SO_4$). The solution was concentrated in a syrup which was crystallised from ether-light petroleum to give (2)(3.5 g, 60%) m.p 115°–117°.$[\alpha]_D +58.5°$ (c 1.02, chloroform); n.m.r. data: $\tau 4.88$ (d,$J_{1,2}$ 3.8 Hz, H-1); 5.22 (q,$J_{2,3}$ 9.5 Hz,H-2); 4.35 (t,$J_{3,4}$ 9.5 Hz, H-3); 6.27 (t,$J_{4,5}$ 9.5 Hz, H-4); 4.53 (s, benzylic); 6.54 (s, OCH$_3$); 7.92 (s, OAc); 2.54–2.78 (aromatic protons).

Anal. Calc. for $C_{16}H_{19}ClO_9S$: C, 45.5; H, 4.53. Found: C, 45.6; H, 4.64.

(b) Methyl 3-O-acetyl-4,6-O-benzylidene-2-chloro-2-deoxy-α-D-mannopyranoside (3)

A solution of (2) (15 g) in hexamethylphosphoric triamide (150 ml) was treated with lithium chloride (15 g) at about 70° for 2.5 h. The reaction mixture was allowed to attain ambient temperature and then poured into ice-water. The precipitate formed was filtered off and taken up in ether, dried ($Na_2SO_4$) and concentrated. The syrupy residue was eluted from a column of silica gel (200 g) using ether-light petroleum (1:2, v/v) to afford (3) (9 g, 74%). $[\alpha]_D +3.6°$ (c 1.16, chloroform); N.m.r. (100 MHz) data: $\tau 5.17$ (d, $J_{4,5}$ 8.8 Hz, H-4); 4.46 (s, benzylic proton); 6.61 (OMe); 7.91 (OAc); 2.50–2.76 (aromatic protons). Mass spectral data: m/e 342 (a), 341 (a), 193 (a), 149, 133 a, 105 a.

Anal. Calc. for $C_{16}H_{19}ClO_6$: C, 56.1; H, 5.59; Cl, 10.3; Found: C, 56.8; H, 5.9; Cl, 10.2.

(c) Methyl 3-O-acetyl-2-chloro-2-deoxy-α-D-mannopyranoside (4).

A solution of (3) (8 g) in 60% aqueous acetic acid (150 ml) was heated at about 80° for 4 h. T.l.c. (ether-light petroleum, 5:1) showed a slow-moving major product. The solution was concentrated by co-distillation with toluene and the resulting syrup was eluted from a column of silica gel (200 g) using ether-light petroleum (4:1 v/v) to give (4) (4 g, 67%), m.p. 105°–106° (from ether-light petroleum), $[\alpha]_D +27.7°$ (c 1.04, chloroform). N.m.r. (100 MHz data: $\tau 5.14$ (d,$J_{1,2}$ 1.5 Hz, H-1); 5.57 (q, $J_{2,3}$ 3.5 Hz, H-2); 4.78 (q, $J_{3,4}$ 9.5 Hz, H-3); 5.87 (t, $J_{4,5}$ 9.5 Hz, H-4); 6.06–6.38 (H-5, H-6); 6.56 (OMe); 7.84 (OAc). After addition of trichloroacetylisocyanate: $\tau 5.13$ (d, $J_{1,2}$ 1.5 Hz H-1); 4.48–4.71 (H-3,H-4); 5.45–5.60 (H-2, H-5, H-6); 6.54 (OMe); 7.90 (OAc); 1.36 (NH); 1.41 (NH).

Anal. Calc. for $C_9H_{15}ClO_6$: C, 42.5; H, 5.94; Cl, 13.9. Found: C, 42.4; H, 5.91; Cl, 13.7.

(d) Methyl 3,4,6-tri-O-acetyl-2-chloro-2-deoxy-α-D-mannopyranoside (5).

A solution of (4) (3 g) in pyridine (20 ml) was treated with acetic anhydride (3 ml) at room temperature for 24 h. T.l.c. (ether-light petroleum, 5:1) showed a fast-moving product. The solution was concentrated by co-distillation with toluene to give (5)(3.2 g, 80%) as a syrup. $[\alpha]_D+35.0°$ (C 1.13, chloroform). N.m.r. data $\tau 5.18$ (d, $J_{1,2}$ 1.5 Hz, H-1); 5.66 (q,$J_{2,3}$ 3.0 Hz, H-2); 4.54–4.78 ( H-3, H-4); 6.06 (m,H-5); 5.84 (m, H-6) 6.62 (s, OMe); 7.95, 7.97, 8.00 (3s, OAc).

Anal. Calc. for $C_{13}H_{19}ClO_8$: C, 46.1; H, 5.65; Cl. 10.47 Found: C, 46.6; H, 5.82; Cl, 9.79.

(e) Methyl 2-chloro-2-deoxy-α-D-mannopyranoside (6)

A solution of (5) (1 g) in dry methanol (50 ml) was treated with a catalytic amount of sodium methoxide at room temperature for 24 h. T.l.c. (chloroform-methanol, 6:1) showed one product. The solution was deionised by shaking with Amberlyst—15 resin (Trade Mark) and concentrated to give (6) (0.57 g, 90%) as a syrup $[\alpha]_D+59.9$ (c 1.05, water).

Anal. Calc. for $C_7H_{13}ClO_5$: C, 39.5; H, 6.16; Cl, 16.7 Found: C, 40.6; H, 6.34; Cl, 15.6.

(f) 2-chloro-2-deoxymannose

The methyl 2-chloro-2-deoxy-mannopyranoside (6) was dissolved in the minimum of methanol and the pH adjusted to 10 by addition of 1 molar sodium methoxide. The solution was kept for 2–5 hours at room temperature and evaported to give the 2-chloro-2-deoxy mannose in about 90% yield.

Comparative Example

Reaction of Methyl 3-O-acetyl-4,6-O-benzylidene-α-D-glucopyranoside 2-chlorosulphate (2) with lithium bromide, sodium azide, sodium chloride, and sodium benzoate as nucleophilic reagents. In a typical reaction, (2) (1 g) was treated with the nucleophilic reagent (1 g) in hexamethylphosphoric triamide (15 ml) at about 70° for 6 h. The reaction was worked up as described for (3). T.l.c. (ether-light petroleum, 5:1) showed that the reaction product was coincident with an authentic sample of Methyl 3-O-acetyl-4,6-O-benzylidene-α-D-glucopyranoside (1)(R. W. Jeanloz and D. A. Jeanloz, J. Am. Chem. Soc., 79 (1957) 2579–2583.) The ether extract was concentrated to give the crystalline (1) as the major product. N.m.r. (100 MHz) data $\tau 5.21$ (d, $J_{1,2}$ 3.5 Hz, H-1); 6.40 (q, $J_{2,3}$ 9.5 Hz, H-2); 4.68 (t, $J_{3,4}$ 9.5 Hz, H-3); 4.54 (s, benzilic); 2.54–2.78 (m, 5H, $C_6H_5$); 6.56 (s, 3H, $OCH_3$); 7.90 (s, 6H, Ac).

EXAMPLE 2

1′,2-Dichloro-1′,2-dideoxymannosucrose (a) 1′,2-Dichloro-1′,2-dideoxymannosucrose hexa-acetate A solution of 3,4,6,3′,4′,6′-hexa-O-acetylsucrose (R. W. Jeanloz and D. A. Jeanloz, J.Am.Chem.Soc., 79 (1957) 2579–2583) (5.4 g) in pyridine (27 ml) and chloroform (80 ml) was treated with sulphuryl chloride (6 ml) at −70° for 2 h. The reaction was worked up at −40° as for compound (3) in Example 1. The dichloromethane extract showed one product t.l.c. (ether-light petroleum 7:1). The solution was concentrated to give a syrup (7 g) which was then treated with lithium chloride (5 g) in hexamethylphosphoric triamide (80 ml) at 80° for 20 h. The mixture was poured on to ice-water, the precipitate was collected and washed thoroughly with water. The solid residue was taken up in ether, dried ($Na_2SO_4$), concentrated and purified by elution through a column of silica gel using ether to give the hexaacetate (4.2 g, 73%) as a syrup $[\alpha]_D−17.2°$ (c 1.2, chloroform). N.m.r. (220 MHz, in deuterobenzene) date: $\tau 4.20$ (d,$J_{1,2}$2.0 Hz, H-1); 6.61 (q, 2 protons, H-1′); 4.24 (d,$J_{3',4'}$7.0 Hz, H-3′); 4.35 (t,$J_{4',5'}$7.0 Hz, H-4′). Mass spectral data: m/e 307, 187, 145.

Anal. Calc for $C_{24}H_{32}Cl_2O_{15}$: C, 45.7; H, 5.11; Cl, 11.2 Found: C, 45.8; H, 5.21; Cl, 11.5

(b) 1′,2-Dichloro-1′,2-diodeoxymannosucrose

A solution of the hexaacetate (2.3 g) in dry methanol (100 ml) was treated with a catalytic amount of sodium methoxide at room temperature for 4 h. T.l.c. (dichloromethane-methanol 2:1) showed one slow-moving product. The solution was deionised with Zerolite DM-F (Trade Mark) and concentrated by co-distillation with methanol to give 1′,2-dichloro-1′,2-dideoxymannosucrose (960 mg, 67%) as a syrup, $[\alpha]_D+23.1°$ (c 1.0, methanol).

Anal. Calc. for $C_{12}H_{20}Cl_2O_9$: C, 38.0; H, 5.32; Cl, 18.7. Found: C, 37.2; H, 5.22; Cl, 17.6.

EXAMPLE 3

2-Chloro-2-deoxy-mannosucrose (a) Reaction of 3,4,6,3′,4′,6′-hexa-O-acetylsucrose with benzoyl chloride A solution of 3,4,6,3′,4′,6′-hexa-O-acetylsucrose (14.0 g) in pyridine (300 ml) and chloroform (150 ml) was cooled to −50° and benzoyl chloride (9 ml) was added dropwise. The reaction was stirred at −50° for 2 hours, and then poured into iced water. The product was extracted into methylene chloride (2×500 ml) which was washed successively with water, aqueous sodium bicarbonate, and water. Concentration of the organic layer afforded a syrup which was eluted from a silica gel column using ether-light petroleum 4:1 to give initially 2,1′-di-O-benzoylsucrose hexa-acetate (12), 0.35 g, 2%) $[\alpha]_D+67.6°$ (c 1.05, chloroform). N.m.r. data ($CDCl_3$): $\tau 4.08$ (d,$J_{1,2}$ 3.0 Hz, H-1); 4.88 (q, $J_{2,3}$ 9.5 Hz, H-2); 4.27 (t, $J_{3,4}$ 9.5 Hz, H-3); 4.81 (t, $J_{4,5}$ 9.5 Hz, H-4); 4.46 (d, $J_{3',4'}$ 5.5 Hz, H-3′); 4.64 (t, $J_{4',5'}$ 5.5 Hz, H-4′); 1.90–2.80 (10 protons, 2 Bz); 7.89–8.10 (18 protons, 6 Ac). Mass spectral data: m/e 393, 273, 231, 169, 105.

Anal. Calc. for $C_{38}H_{42}O_{19}$: C, 56.9; H, 5.27. Found: C, 57.2; H, 5.39.

Further elution of the column afforded 3,4,6,3′,4′,6′-hexa-O-acetyl-1′-O-benzoylsucrose (13), (6.2 g, 38%). $[\alpha]_D+67.8°$ (c 1.03, chloroform). N.m.r. data ($CDCl_3$): $\tau 4.41$ (d,$J_{1,2}$ 3.0 Hz, H-1); 6.32 (q, $J_{2,3}$9.5 Hz, H-2); 4.81 (t,$J_{3,4}$ 9.5 Hz; H-3); 4.99 (t, $J_{4,5}$ 9.5 Hz, H-4); 4.46 (d, $J_{3',4'}$ 5.5 Hz, H-3′); 4.50 (t,$J_{4',5}=$ 5.5 Hz, H-4′); 1.94–2.67 (5 protons, Bz); 7.88–8.00 (18 protons, 6 Ac).

After addition of trichloroacetyl isocyanate to the n.m.r. sample: $\tau 4.29$ (d, $J_{1,2}$ 3.0 Hz, H-1); 5.05 (q, $J_{2,3}$ 9.5 Hz, H-2); 4.62 (t, $J_{3,4}$ 9.5 Hz, H-3); 4.96 (t, $J_{4,5}$ 9.5 Hz, H-4); 4.69 (d, $J_{3',4'}$ 5.5 Hz, H-3′); 4.77 (t, $J_{4',5'}$ 5.5 Hz, H-4′); 0.92 (s, 1 proton, NH); 2.10–2.72 (5 protons, Bz); 7.70–8.06 (18 protons, 6 Ac)

Anal. Calc. for $C_{31}H_{38}O_{18}$: C, 53.3; H, 5.48. Found: C, 52.9; H, 5.45.

Unreacted 3,4,6,3',4',6'-hexa-O-acetylsucrose (6.7 g, 48%) was obtained on washing the silica gel column with ether.

(b)
3,4,6,3',4',6-Hexa-O-acetyl-1'-O-benzoylsucrose-2-chlorosulphate (14)

A solution of 3,4,6,3',4',6'-hexa-O-acetyl-1'-O-benzoylsucrose (13), (5.2 g) in a mixture of pyridine (25 ml) and chloroform (80 ml) was treated with sulphuryl chloride (6 ml) at −70° for 3 hours. The reaction was worked up at −40° as described in Example 1. The dichloromethane extract revealed a single product on t.l.c. (ether-light petroleum 4:1) and was concentrated to give (14) as a dry syrup. (5.4 g, 91%) $[\alpha]_D+61.2$ (c 1.07, chloroform. N.m.r. (100 MHz data: $\tau$4.08 (d, $J_2$ 3.5 Hz, H-1); 5.19 (q, $J_{3'}$ 5.5 Hz, H-3'); 4.62 (t, $J_{4',5'}$ 5.5 Hz, H-4'); 1.95-2.64 (5 protons, Bz); 7.88-7.9; (18 protons, 6 Ac).

Anal. Calc. for $C_{31}H_{37}ClO_{20}S$: C, 46.7; H, 4.68; Cl, 4.45; S, 4.02. Found: C, 46.9; H, 4.66; Cl, 4.74; S, 4.98.

(c) 1'-O-Benzoyl-2-chloro-2-deoxymannosucrose hexa-acetate (15)

Lithium chloride (5 g) was added to a solution of (14) (4.1 g) in hexamethylphosphoric triamide (80 ml) and stirred at 80° for 24 hours. The reaction mixture was worked up as described in the preparation of compound (3)—Example 1. Elution of the syrupy product mixture from a column of silica gel (100 g) using ether-light petroleum (1:1) gave (15) (1.7 g, 49% $[\alpha]_D+7.6°$ (c 0.95, chloroform). N.m.r. (220 MHz data: $\tau$4.08 (d, $J_{1,2}$ 2.0 Hz, H-1); 5.45 (q, $J_{2,3}$ 3.4 Hz, H-2); 2,6,1',6'-Tetrachloro-2,6,1',6'-tetradeoxymannosucrose 4.23 (q, $J_{3,4}$ 9.5 Hz, H-3); 4.13 (q,$J_{4,5}$10.5 Hz, H-4). 4.28 (d,$J_{3',4'}$6.0 Hz, H-3') 4.36 (t,$J_{4,5}$6.0 Hz, H-4'); 2.80-2.90 (m, 5 protons, Bz); 8.14, 8.19, 8.29, 8.34, 8.42, (18 protons, 6 Ac). Mass spectral data: m/e 393b, 307a, 273b, 231b,187a, 145a, 109b.

Anal. Calc. For $C_{31}H_{37}ClO_{17}$: C, 51.9; H, 5.20; Cl, 4,94 Found: C, 52.0; H, 5.27; Cl, 4.92.

(d) 2-chloro-2-deoxymannosucrose

The free 2-chloro-2-deoxymannosucrose was obtained by a process similar to that of Example 1 (f) in approximately 90% yield.

EXAMPLE 4

(a)
2,6,1',6'-Tetrachloro-2,6,1',6'-tetradeoxymannosucrose tetraacetate (16)

A solution of 3,4,3',4'-tetra-O-acetyl-6,6'-dichloro-6,6'-dideoxysucrose (L. Hough, S. P. Phadnis, and E. Tarelli, Carbohydr. Res., 47 (1976) 151-154.) (5 g) in pyridine (25 ml) and chloroform (75 ml) was treated with sulphuryl chloride (2.5 ml) at −75°. The reaction was worked up as described in Example 1 to give the 1',2-bis(chlorosulphate) (5.4 g, 80%).

This compound (4 g) was then treated with lithium chloride (4 g) in hexamethylphosphoric triamide (30 ml) at 80° for 20 h. The reaction was worked up as described in Example 2(a) to give a syrup. Elution of the syrup from a column of silica gel (100 g), using ether-light petroleum (1:1) gave the 2,6,1',6'-tetrachloride (16)(2.7 g, 85%) as a syrup $[\alpha]_D-16.7°$ (c 1.01, chloroform). N.m.r. data (CDCl$_3$): $\tau$4.40 (d,$J_{1,2}$ 2.0 Hz, H-1); 5.57 (q,$J_{2,3}$ 4.0 Hz, H-2); 4.34-4.60 (m, 2 protons, H-3', H-4'); 6.10-6.51 (6 protons, H-6, H-1', H-6'); 7.78-7.88 (12 protons, 4 Ac). Mass spectral data m/e 283, 223, 163.

Anal. Cal. for $C_{20}H_{26}Cl_4O_{11}$: C, 41,1; H, 4.49; Cl, 24.3. Found: C, 42.1; H, 4.75; Cl, 24.1.

(b)
2,6,1',6'-Tetrachloro-2,6,1',6'-tetradeoxymannosucrose (17)

A solution of (16) (1 g) in dry methanol was treated with a catalytic amount of sodium methoxide at room temperature for 20 h. The solution was deionised with Amberlyst—15 resin and concentrated to afford (17)(0.64 g, 90%) as a syrup, $[\alpha]_D+22.4°$ (c 0.93, methanol).

Anal. Calc. for $C_{12}H_{18}Cl_4O_7$: C, 34.6; H, 4.36. Found: C, 35.2; H, 4.68.

EXAMPLE 5

2,1'-Dichloro-2,1'-dideoxymannosucrose (0.8 g) was dissolved in pyridine (80 ml). The solution was cooled to 0° C. and triphenylphosphine (3.33 g) was added, followed by addition at 0° C. of carbon tetrachloride (0.60 ml). The resulting mixture was protected from moisture and stirred. After keeping the mixture at the desired temperature, 70°-80° C., for 50 minutes, T.L.C. revealed a faster moving component and the absence of the starting material. Methanol (80 ml) was then added to decompose any excess of reagent. The solvent was removed by evaporation and the residue was dissolved in pyridine and acetylated with acetic anhydride to isolate the product as tetrachloride tetraacetate which was then deacetylated in the conventional manner.

We claim:
1. A process for the preparation of a 2-chloro-2-deoxy-mono-, di- or oligo-saccharide, in which a mono-, di-, or oligo-saccharide derivative having a free hydroxy group in at least the 2-position and having the hydroxy group in at least the 1- and 3-positions protected from chlorination, is reacted with sulphuryl chloride in the presence of an organic base in a chlorinated hydrocarbon solvent at a temperature below −40° C. to form a chlorosulphate derivative with a chlorosulphate group in at least the 2-position, which chlorosulphate derivative is then reacted with lithium chloride in the presence of a polar aprotic solvent to replace chlorosulphate groups with chlorine atoms to form a chlorodeoxy derivative, which chlorodeoxy derivative is then freed of unwanted protecting groups.

2. A process according to claim 1, in which the organic base is a tertiary amine.

3. A process according to claim 2, in which the base is a pyridine compound.

4. A process according to claim 1, in which the chlorinated hydrocarbon is chloroform.

5. A process according to claim 4, in which chloroform and pyridine are used in a volume ratio of 2.5:1 to 3.5:1.

6. A process according to claim 1, in which the temperature of reaction with sulphuryl chloride is about −70° C.

7. A process according to claim 1, in which the aprotic solvent is hexamethylphosphoric triamide.

8. A process according to claim 1, in which the reaction with lithium chloride is effected at a temperature of from 40° to 100° C.

9. A process according to claim 8, in which the temperature is about 70° C.

10. A process according to claim 1, in which the saccharide starting material has hydroxy groups protected by ester or ether groups or has hydroxy groups substituted by chlorine atoms.

11. A process according to claim 1, in which the saccharide starting material comprises at least one pentose or hexose ring in the pyranose or furanose form.

12. A process according to claim 11 in which the saccharide starting material is a glucose, sucrose or raffinose derivative.

13. A compound of the general formula

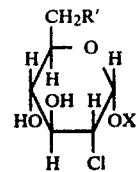

where X represents an aglycone of the general formula

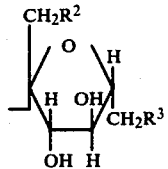

where $R^2$ is chlorine and $R^3$ is the same as $R'$ and is chlorine or hydroxy.

14. 2,1'-Dichloro-2,1'-dideoxymannosucrose.
15. 2-Chloro-2-deoxymannosucrose.
16. 2,1',6,6'-Tetrachloro-2,1',6,6'-tetradeoxymannosucrose.

* * * * *

UNITED STATES PATENT AND TRADEMARK OFFICE
CERTIFICATE OF CORRECTION

PATENT NO. : 4,262,115

DATED : April 14, 1981

INVENTOR(S) : Riaz A. Khan et al.

It is certified that error appears in the above—identified patent and that said Letters Patent is hereby corrected as shown below:

ON THE TITLE PAGE: Assignee should read -- Talres Development (N.A.) N.V. --.

Column 2, line 24, "glycose" should read -- glucose --;

line 67, after "invention" insert -- , --.

Column 5, line 10, "C" should read -- c --.

Column 6, line 15, "diodeoxymannosucrose" should read -- dideoxymannosucrose --;

line 59, "$J_{4',5} = 5.5$" should read -- $J_{4',5'}$ 5.5 --.

UNITED STATES PATENT AND TRADEMARK OFFICE
CERTIFICATE OF CORRECTION

PATENT NO. : 4,262,115

DATED : April 14, 1981

INVENTOR(S) : Riaz A. Khan et al.

It is certified that error appears in the above—identified patent and that said Letters Patent is hereby corrected as shown below:

Column 7, line 9, dlelete the comma;

line 41, "4,94" should read -- 4.94 --.

Column 8, line 3, "41,1" should read -- 41.1 --.

Signed and Sealed this

Twenty-ninth Day of September 1981

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,262,115
DATED : April 14, 1981
INVENTOR(S) : Riaz A. Khan, Michael R. Jenner It is certified that error appears in the above-identified patent and that said Letters Patent are hereby corrected as shown below:

For the assignee read -- Talres Development (N.A.) N.V. --

Column 2, line 24, "glycose" read -- glucose --; line 67, after "invention" read -- , --.

Column 3, for the formula at the top (lines 1-9), read

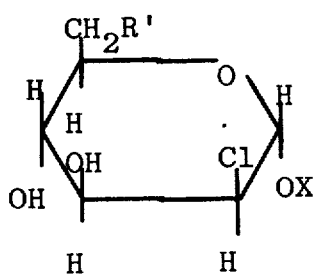

Column 5, line 10, for "C" read -- c --.

Column 6, line 15, for "diodeoxymannosucrose" read -- dideoxymannosucrose --; line 59, for "$J_{4',5} = 5.5$" read -- $J_{4',5'}$ 5.5 --.

UNITED STATES PATENT AND TRADEMARK OFFICE
CERTIFICATE OF CORRECTION

PATENT NO. : 4,262,115

DATED : April 14, 1981

INVENTOR(S) : Riaz A. Khan, Michael R. Jenner

It is certified that error appears in the above-identified patent and that said Letters Patent are hereby corrected as shown below:

Column 7, line 9, delete the comma; line 41, for "4,94" read -- 4.94 --.

Column 8, line 3, for "41,1" read -- 41.1 --.

Column 10, for the formula at the top (lines 1-9) read

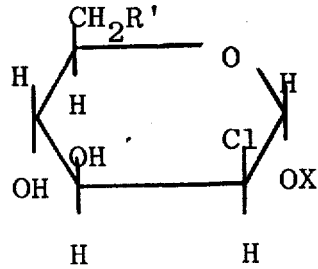

Signed and Sealed this

Twenty-seventh Day of October 1981

[SEAL]

Attest:

GERALD J. MOSSINGHOFF

Attesting Officer     Commissioner of Patents and Trademarks